United States Patent [19]

Johnson et al.

[11] Patent Number: 5,512,547

[45] Date of Patent: Apr. 30, 1996

[54] PHARMACEUTICAL COMPOSITION OF BOTULINUM NEUROTOXIN AND METHOD OF PREPARATION

[75] Inventors: Eric A. Johnson; Michael C. Goodnough, both of Madison, Wis.

[73] Assignee: Wisconsin Alumni Research Foundation, Madison, Wis.

[21] Appl. No.: 322,624

[22] Filed: Oct. 13, 1994

[51] Int. Cl.$^6$ .............................. A61K 38/00; C07K 1/00
[52] U.S. Cl. ................................ 514/21; 514/2; 530/350; 530/363; 530/364; 530/825
[58] Field of Search ........................... 514/21.2; 530/350, 530/363, 364, 825

[56] References Cited

PUBLICATIONS

Goodnough et al, *Applied and Environmental Microbiology*, vol. 58, No. 10, pp. 3426–3428, Oct. 1992.

Schantz, E. J. and Scott, A. B., Biomedical Aspects of Botulism, Academic Press, Inc., pp.143–150 (1981).

Schantz, E. J., and Kautter, D. A., *Journal of the Association of Official Analytical Chemists*, vol. 61, pp. 96–99 (1978).

Melling et al., "Clostridium Botulinum Toxins: Nature and Preparation for Clinical Use." Eye, vol. 2, 1988, pp.–16–23.

Hambleton et al. "Production, Purification and Toxoiding of Clostridium Botulinum Type A Toxin", Biomedical Aspects of Botulism, Academic Press, Inc., (1981) pp. 247–260.

*Primary Examiner*—Christina Y. Chan
*Assistant Examiner*—Abdel A. Mohamed
*Attorney, Agent, or Firm*—Quarles & Brady

[57] ABSTRACT

Pharmaceutical compositions of botulinum neurotoxin containing higher specific toxicity and increased stability at higher temperatures than currently available preparations.

3 Claims, No Drawings

PHARMACEUTICAL COMPOSITION OF BOTULINUM NEUROTOXIN AND METHOD OF PREPARATION

FIELD OF THE INVENTION

The present invention relates to botulinum toxin. More particularly, it relates to novel pharmaceutical compositions containing botulinum toxin and a method for preparing the compositions.

BACKGROUND OF THE INVENTION

The most serious form of bacterial food poisoning is botulism which is caused by neurotoxins produced by *Clostridium botulinum*. The toxins are usually preformed by the causative organism in foods and subsequently absorbed through the intestinal tract and transported via the circulatory system to motor nerve synapses where their action blocks normal neural transmissions. Various serotypes of *C. botulinum* produce neurotoxins with similar toxic activity but which differ antigenically. Serotype A toxin is the predominant cause of botulism in the United States while type B toxin is the most prevalent in Europe.

Crystalline type A botulinum toxin complex was prepared in 1979 by E. J. Schantz of the Food Research Institute/ Department of Food Microbiology and Toxicology at the University of Wisconsin-Madison. It has been used medically to treat hyperactive muscle disorders such as strabismus, blepharospasm, and spasmodic torticollis. Treatment involves injection of nanogram quantities of the toxin directly into the hyperactive muscles. The toxin inhibits the release of acetylcholine across the synaptic junction causing a decrease in the activity of the injected muscles.

Type A neurotoxin produced by *C. botulinum* is present as part of a complex of at least seven different noncovalently bound proteins. High quality type A toxin complex has a specific toxicity of $3 \times 10^7$ mouse intraperitoneal 50% lethal doses ($LD_{50}$) per mg. The purified neurotoxin, that is the neurotoxin that has been chromatographically separated from the other proteins of the toxin complex, has a specific toxicity of $9 \times 10^7$ to $1 \times 10^8$ $LD_{50}$ per mg. In the medical field, a unit (U) is considered to be 1 $LD_{50}$. Toxin titers are determined in female, white mice, 18–22g in weight according to the method of Schantz and Kautter as described in Association of Official and Analytical Chemistry, vol. 61, p. 96, (1978).

A major drawback to the use of botulinum toxin in treatment of hyperactive muscle disorders is development of antibodies or other types of immunity by patients. The toxin is recognized by patient's immune systems as foreign and stimulates antibody production. This renders treatment of the various hyperactive muscle disorders with botulinum toxin ineffective. One way to reduce the number of patients developing neutralizing antibodies would be to develop a more shelf-stable product with a higher specific activity following lyophilization. Such a formulation would result in a product that is not as antigenic as the currently available product and lesser quantities of toxin would be required for treatment.

Botulinal toxin is very susceptible to denaturation due to surface denaturation, heat, and alkaline conditions. Lyophilization or freeze-drying of botulinal toxin is the most economically sound and practical method of distributing the product in a form that is stable and readily used by the clinician. The current commercial type A botulinal toxin product is made by combining up to 500 ng/ml of type A toxin complex in 5.0 mg/ml human serum albumin (HSA) with 9.0 mg/ml sodium chloride at a pH of 7.3. After dissolution, 0.1 ml is dried to obtain 100±30 active U of toxin, 0.5 mg of HSA, and 0.9 mg of sodium chloride per vial. This product has a saline concentration of 0.9% when reconstituted in 1.0 ml of $dH_2O$. The current commercial formulation which employs the toxin complex has a specific toxicity of about 2.5 U/ng after drying BOTOX®, crystalline botulinum toxin complex, Allergon, Inc. of Irvine, Calif. The considerable loss (up to 90%) of activity during drying causes the formation of inactive toxin that serves as a toxoid inciting antibody formation.

A rabbit model in which repetitive injections of various type A toxin preparations have been given to simulate the treatment of a focal dystonia has been used to assess the immunogenicity of various toxin preparations. The model consists of injecting albino rabbits with sublethal doses of the toxin over a period of time and assaying the serum of the animals for the ability to neutralize a small but carefully quantitated amount of purified type A toxin. Our results show that the product presently available in the United States which has the lowest specific toxicity of all preparations tested is the most antigenic of all the preparations tested to date. These results indicate that high specific activity preparations reduce the probability of patients developing neutralizing antibodies. It obviously would be desirable to have higher specific activity preparations than those currently available.

The current commercial product must be stored at a temperature of −10° C. or less to maintain the labelled potency for the one year shelf life. It also would be advantageous to have a product that could be stored at higher temperatures (i.e. room temperature). This would facilitate more practical shipping and storage of the toxin.

BRIEF SUMMARY OF THE INVENTION

We have discovered that pharmaceutical compositions made from a liquid formulation containing essentially pure botulinum type A neurotoxin, human serum albumin (HSA), and trehalose provides for the improved recovery of active toxin following lyophilization (>80%). The use of the pure neurotoxin instead of the toxin complex, which is used commercially, reduces the amount of toxin required to obtain the necessary number of active U per vial as mandated by the U.S. Food and Drug Administration. This improvement also reduces the amount of inactive toxin (toxoid) in each vial and thereby lessens the possibility of antibody formation after injection of the preparation into patients.

We also have discovered that the compositions obtained by adding trehalose to the pre-lyophilization formula increases the glass transition temperature of the dried material and thereby increases the usable storage temperature. The addition of the trehalose surprisingly enhances the temperature stability of the dried toxin and lessens both the risk of loss in potency with corresponding degradation during storage and shipment with a consequent increase in antigenic potential due to temperature abuse. In addition to trehalose, we have discovered that the polyhydroxy compound maltotriose and possibly other polyols can be used.

DESCRIPTION OF PREFERRED EMBODIMENT

The preferred pharmaceutical compositions of the present invention have the following composition:

Botulinum Type A Neurotoxin (>95% purity)
Trehalose, 10 mg/vial
Serum albumin, 0.5 mg/vial
Water for Injection, 0.1–0.5 ml In addition to human serum albumin, other known stabilizing proteins including bovine serum albumin, can be used in the compositions of the present invention.

The Hall A strain of type A *C. botulinum* (deposited with the ATCC) is used to produce type A toxin. This strain is routinely used for production of type A botulinum toxin due to high toxin titers and the rapid onset of cell lysis (usually within 48 h).

For toxin production, cultures of the Hall A strain are grown statically in 10–20 liter volumes of toxin production medium (TPM) consisting of 2.0% NZ amine or TT (Sheffield Laboratories, Norwich, N.Y.), 1.0% yeast extract (Difco), and 0.5% dextrose, pH 7.37.4, for 5–7 days at 37° C.

To prepare essentially pure type A neurotoxin, the type A toxin complex is first purified according to the method described in the Ph.D. thesis of M. C. Goodnough (Goodnough, M. C. 1994, Characterization and stabilization of *Clostridium botulinum* toxin for medical use. Ph.D. thesis, UW-Madison, as adapted from Tse et al. 1982)

Type A neurotoxin is purified from the associated non-toxic proteins of the complex by a modification of the method of Tse et al. (1982) (Goodnough, M. C., 1994, Thesis, UW, Wisconsin). Toxin complex is recovered from the DEAE-Sephadex A50 (Sigma Chemical Co., St. Louis, Mo.), pH 5.5, column and is precipitated by addition of 39 g of solid ammonium sulfate/100 ml. The precipitated toxin complex is collected by centrifugation, dialyzed against 25 mM sodium phosphate, pH 7.9, and applied to a DEAE-Sephadex A50 column equilibrated with the same buffer. Toxin is separated from the non-toxic proteins of the complex and eluted from the column with a linear 0–0.5M sodium chloride gradient. Partially purified neurotoxin is recovered from the DEAE-Sephadex A50 column at pH 7.9 and dialyzed against 25 mM sodium phosphate, pH 7.0. The dialyzed toxin is applied to SP-Sephadex C50 (Sigma Chemical Co.) in 25 mM sodium phosphate, pH 7.0. Contaminating material does not bind to the column under these conditions. The neurotoxin is eluted with a linear 0–0.25M sodium chloride gradient. The neurotoxin can be further purified by metal affinity chromatography, gel filtration or other methods of protein chromatography.

For lyophilization, toxin samples are diluted in the excipients (stabilizing compounds) to be tested (Sigma Chemical Co.), 0.1 ml or 0.5 ml aliquoted into 2 ml glass vials (Fisher Scientific Co., Pittsburgh, Pa.), the Teflon lined screw cap closures fastened loosely, and the samples are quickly frozen in liquid nitrogen. The frozen samples are placed into a lyophilization flask which is then immersed in liquid nitrogen. The flask is then connected to a laboratory freeze-drier (Virtis Freezmobile 12, Virtis Co., Inc., Gardiner, N.Y.). When the pressure drops below ca. 60 mTorr, the liquid nitrogen jacket is removed. Pressure is maintained at or below 30–60 mTorr and condenser temperature constant at −60° C. Samples are allowed to come to room temperature and drying continued at ambient temperature over the next 18–24 h. At that time the flask is removed and the vials tightly capped. Vials were assayed for toxicity and recovery calculated within 1–3 days (adapted from Goodnough and Johnson, 1992).

Vials of lyophilized type A neurotoxin and type A toxin complex were stored at various temperatures to investigate the effect of added excipients on the shelf-stability of the dried material. In these cases, the tightly capped vials were placed into plastic bags, sealed and stored at various temperatures (−20°, 4°, or 37° C.) and the contents assayed for toxicity at various time points. The lyophilized preparations were usually reconstituted in 1.0 ml of distilled water. The use of 0.85% saline for reconstitution gave equivalent results. The white cake dissolved immediately and was mixed by gentle inversion of the vials. The resulting solution was transparent and contained no particulates. This solution was titrated by the same method used for the prelyophilization solution. The percent recovery (calculated as number of mouse intraperitoneal lethal doses per vial after lyophilization divided by the number of mouse intraperitoneal lethal doses before lyophilization×100) represent averages of trials done in at least duplicate. The variation in independent assays was ca. ±20%.

The percent recoveries of active toxin determined within 2–3 days following lyophilization of type A toxin complex and purified type A neurotoxin in various excipient combinations are shown in Tables 1 and 2.

The primary advantages of preferred compositions of the present invention are their high percentage recovery of biologically active neurotoxin and their long-term stability (shelf life) at temperatures above 0° C. In contrast, the current commercial product has a low percentage recovery of biologically active neurotoxin and must be stored at temperatures of −10° C. or less.

TABLE 1

Effect of excipients on recovery of toxicity of *Clostridium botulinum* type A toxin complex after lyophilization of 0.1 ml of each solution.

| Excipients | Starting Toxin concentration[a] | pH | % recovery[b] |
| --- | --- | --- | --- |
| sodium phosphate[c] | 50, 100, 1,000 | 5.0, 6.0, 6.8 | <10 |
| bovine serum albumin/sodium chloride[d] | 100 | 6.4 | 10 |
| bovine serum albumin[e] | 100, 1,000 | 6.4 | 88, 75 |
| bovine serum albumin/citrate[f] | 100, 1,000 | 5.0 | >90, >90 |
| bovine serum albumin/phosphate[g] | 100, 1,000 | 5.5 | >90, >90 |
| bovine serum albumin/phosphate[g] | 1,000 | 7.3 | 60 |
| bovine serum albumin/phosphate[h] | 1,000 | 6.0 | >90 |

TABLE 1-continued

Effect of excipients on recovery of toxicity of *Clostridium botulinum* type A toxin complex after lyophilization of 0.1 ml of each solution.

| Excipients | Starting Toxin concentration[a] | pH | % recovery[b] |
|---|---|---|---|
| human serum albumin[i] | 100, 1,000 | 6.4–6.8 | >90, >90 |
| alpha-lactalbumin[j] | 1,800 | 6.1 | >78 |
| lysozyme[j] | 1,800 | 5.3 | >78 |
| gelatin[j] | 1,800 | 6.3 | >78 |
| bovine serum albumin/trehalose[k] | 500 | 5.7 | >90 |
| bovine serum albumin/sucrose[l] | 325 | 6.6 | 65 |
| bovine serum albumin/maltotriose[m] | 250 | 7.0 | >80 |

[a]Type A mouse lethal doses/vial before lyophilization;
[b]% recovery = (number mouse lethal doses after lyophilization/number mouse lethal doses prior to lyophilization) × 100;
[c]50 mM sodium phosphate;
[d]bovine serum albumin (5.0 mg/ml), sodium chloride (9.0 mg/ml);
[e]bovine serum albumin (9.0 mg/ml);
[f]bovine serum albumin (9.0 mg/ml), 50 mm sodium citrate;
[g]bovine serum albumin (9.0 mg/ml), 50 mm sodium phosphate;
[h]bovine serum albumin (9.0 mg/ml), 50 mm potassium phosphate;
[i]human serum albumin (9.0 mg/ml);
[j]concentration = 9.0 mg/ml;
[k]9.0 mg/ml bovine serum albumin, 100 mg/ml trehalose;
[l]9.0 mg/ml bovine serum albumin, 250 mg/ml sucrose;
[m]9.0 mg/ml bovine serum albumin, 100 mg/ml maltotriose. (adapted from Goodnough and Johnson, 1992).

TABLE 2

Recovery of activity following lyophilization of purified *Clostridium botulinum* type A neurotoxin.

| Excipient combination | Starting Toxin concentration[b] | pH | % recovery[c] |
|---|---|---|---|
| bovine serum albumin | 200 | 6.4 | 90 |
| human serum albumin | 1,000 | 6.4 | 90 |
| bovine serum albumin, trehalose | 500 | 5.7 | >90 |
| bovine serum albumin, sucrose | 325 | 6.6 | 50 |
| bovine serum albumin, maltotriose | 250 | 7.0 | >80 |

[a]bovine and human serum albumin concentration was 9.0 mg/ml, carbohydrate concentration was 100 mg/ml in all cases except sucrose which was 250 mg/ml;
[b]mouse intraperitoneal lethal doses/vial;
[c](number of mouse lethal doses/vial after lyophilization, number of mouse lethal doses before lyophilization) × 100.

It was found that the formulations used for lyophilization had a marked effect on the recovery of toxin. The most critical factor was the absence of sodium chloride in the solution in combination with a pH less than 7.0. In the best cases, recovery of active toxin was >90% following lyophilization.

The addition of trehalose in particular, allowed the recovery of active type A neurotoxin following lyophilization and storage at temperatures in excess of those required for storage of the commercially available type A toxin complex (37° C. versus −10° C.).

The antigenicity of various toxin preparations (containing low or high specific toxicities) was evaluated in rabbits by repetitive injection of sublethal doses of toxin simulating treatment of a focal dystonia with botulinal toxin. The samples were standardized to contain the same number of active lethal doses in order that the immune response from the rabbits could be compared. The samples with the highest specific activity were those consisting of purified type A neurotoxin (96 U/ng) while the lowest were the commercially available BOTOX®, crystalline botulinum toxin complex, samples (4.3 U/ng).

Total toxin concentration for each preparation (i.e. both active and inactive) was determined using an enzyme-linked immunosorbent assay (ELISA) specific for type A botulinal toxin. The ELISA assays performed on BOTOX®, crystalline botulinum toxin complex, and ASB indicated that BOTOX®, crystalline botulinum toxin complex, had an average specific toxicity of 4.3 U/ng and ASB had an average specific toxicity of 17.3 U/ng after reconstitution. Type A toxin complex used in these assays had a specific activity of 18 U/ng.

Serum samples were drawn on the days shown in Table 3 and titrated for the ability to neutralize 5.6 U of essentially pure type A neurotoxin. Total toxin concentration (active+inactive) in each preparation was determined by ELISA following reconstitution except in the cases of A neurotoxin and A complex which were not lyophilized.

TABLE 3

| Immune response of rabbits to sub-lethal doses of type A botulinal toxin. | | | | | | |
|---|---|---|---|---|---|---|
| Day | A neurotoxin | A complex | Botox I* | Botox II* | ASB I* | ASB II* |
| | 0 | 0 | 0 | 0 | 0 | 0 |
| | 29 | 28 | 21 | 21 | 21 | 21 |
| | 42 | 35 | 35 | 35 | 35 | 35 |
| | 56 | 56 | 49 | 49 | 49 | 46 |
| | 69 | 69 | 60 (1:1)[a] | 63 (1:1)[a] | 60 (no antibodies detected) | 60 |
| | 88 | 88 | | 77 (1:2) | | 67 |
| | 107 | 109 | | 84 (1:4) | | 81 |
| | 118 | 118 | | | | 95 (1:1)[a] |
| | (No antibodies detected) | (No antibodies detected) | | | | |
| Total ng of toxin: | 0.92 | 5.12 | 18.3 | 25.41 | 4.075 | 6.52 |

*Two separate animal trials labeled I and II are represented.
[a]All antibody samples were titrated against 5.6 mouse lethal doses of purified type A neurotoxin according to the following: 0.5 ml serum + 0.1 ml containing 5.6 $LD_{50}$ type A toxin + 0.6 ml gel-phosphate, pH 6.4. The solution was incubated at room temperature for 30–60 minutes. Two mice per two fold dilution were injected intraperitoneally with 0.5 ml of serum + toxin mixture.
Dilutions which neutralized the toxin challenge are indicated in brackets. The last value in the numerical column indicates the final day of sampling. Numbers in parentheses indicate final dilution which neutralized toxin challenge.

These results show that the immune response of rabbits to botulinal toxin is dependent on concentration of the toxin (active+inactive) injected as well as the number of times the animal is exposed to that concentration. From these results it follows that the higher the specific activity of the lyophilized/reconstituted toxin product, the less antigenic material the patient is exposed to and the smaller the chances of patients developing neutralizing antibodies. Thus, it is advantageous to have pharmaceutical compositions of lyophilized essentially pure neurotoxin which permit the recovery of a high percentage of the starting activity and contain trehalose for storage of the dried product without degradation at temperatures above that of the currently available product are shown.

It will be apparent to those skilled in the art that a number of modifications and changes can be made without departing from the spirit and scope of the present invention. Therefore, it is intended that the invention be limited only by the claims.

We claim:

1. A pharmaceutical composition consisting essentially of:
   (a) isolated, essentially pure type A botulinum neurotoxin;
   (b) serum albumin; and
   (c) an effective amount of trehalose which stabilizes the neurotoxin and improves the shelf life of composition so that it is stable at temperatures up to about 37° C.

2. A composition of claim 1 in which the botulinum neurotoxin has specific toxicity of about 80 U/ng to about 96 U/ng.

3. A lyophilized pharmaceutical composition of type A botulinum neurotoxin which is stable for up to four months at about 37° C. without the neurotoxin losing its potency, said composition consisting essentially of pure type A botulinum neurotoxin and an effective amount of trehalose to stabilize the neurotoxin.

* * * * *